United States Patent
Sone

(10) Patent No.: US 9,039,605 B2
(45) Date of Patent: May 26, 2015

(54) ENDOSCOPE

(71) Applicant: OLYMPUS MEDICAL SYSTEMS CORP., Tokyo (JP)

(72) Inventor: Nobuhiko Sone, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 13/905,579

(22) Filed: May 30, 2013

(65) Prior Publication Data
US 2013/0310649 A1 Nov. 21, 2013

Related U.S. Application Data

(63) Continuation of application No. PCT/JP2012/079989, filed on Nov. 19, 2012.

(30) Foreign Application Priority Data

Dec. 1, 2011 (JP) ................................. 2011-263735

(51) Int. Cl.
*A61B 1/06* (2006.01)
*G02B 23/26* (2006.01)
(Continued)

(52) U.S. Cl.
CPC . *A61B 1/06* (2013.01); *G02B 23/26* (2013.01); *G02B 23/2469* (2013.01); *A61B 1/00096* (2013.01); *A61B 1/07* (2013.01); *G02B 6/0008* (2013.01)

(58) Field of Classification Search
CPC ........................ A61B 1/00096; A61B 1/00167
USPC ............. 600/176, 177, 182; 348/68; 362/574; 385/119; 359/799
See application file for complete search history.

(56) References Cited

U.S. PATENT DOCUMENTS 5,354,322 A * 10/1994 Miyano ........................... 607/88
5,871,440 A * 2/1999 Okada ........................... 600/129
(Continued)

FOREIGN PATENT DOCUMENTS

EP 2 469 322 6/2012
JP 10-288742 10/1998
(Continued)

OTHER PUBLICATIONS

International Search Report, dated Jan. 15, 2013, issued in corresponding International Application No. PCT/JP2012/079989.

*Primary Examiner* — Anhtuan T Nguyen
*Assistant Examiner* — Timothy J Neal
(74) *Attorney, Agent, or Firm* — Kenyon & Kenyon LLP

(57) ABSTRACT

To provide excellent illumination over entire range from near view to distant view to achieve clear observation over entire range from near view to distant view.
Provided is an endoscope including an imaging optical system 3 provided in insertion portion at a distal end thereof and for observing an object to be observed, and a plurality of illumination optical systems 2a, 2b provided in the insertion portion 1 and for distributing the illuminating light emitted from a light source to the object to be observed, the illumination optical systems being directed in the same direction each other to illuminate the same field of view, wherein at least one of the plurality of illumination optical systems is a first illumination optical system 2a having a convex lens, and at least one of the others is a second illumination optical system 2b having a concave lens.

14 Claims, 8 Drawing Sheets

(51) Int. Cl.
    *G02B 23/24*    (2006.01)
    *A61B 1/07*    (2006.01)
    *F21V 8/00*    (2006.01)
    *A61B 1/00*    (2006.01)

(56) References Cited

U.S. PATENT DOCUMENTS

| | | | |
|---|---|---|---|
| 6,184,923 B1 * | 2/2001 | Miyazaki | 348/75 |
| 2001/0003142 A1 * | 6/2001 | Koshikawa | 600/177 |
| 2002/0137985 A1 * | 9/2002 | Ouchi | 600/139 |
| 2006/0052668 A1 | 3/2006 | Homma | |
| 2009/0281385 A1 | 11/2009 | Hatoma | |
| 2009/0287057 A1 * | 11/2009 | Murata et al. | 600/177 |

FOREIGN PATENT DOCUMENTS

| | | |
|---|---|---|
| JP | 11-125773 | 5/1999 |
| JP | 2006-072098 | 3/2006 |
| JP | 2009-291594 | 12/2009 |
| WO | 2011/058912 | 5/2011 |

* cited by examiner

FIG. 4

| ANGLE θ | LIGHT GUIDE FIBER | ILLUMINATION OPTICAL SYSTEM 2a | ILLUMINATION OPTICAL SYSTEM 2b | COMBINED ILLUMINATION OPTICAL SYSTEM 2c |
|---|---|---|---|---|
| 0 | 1.00 | 1.00 | 1.00 | 1.00 |
| 5 | 0.97 | 1.01 | 0.99 | 1.00 |
| 10 | 0.94 | 0.99 | 0.98 | 0.98 |
| 15 | 0.85 | 0.98 | 0.97 | 0.97 |
| 20 | 0.67 | 0.98 | 0.95 | 0.96 |
| 25 | 0.46 | 0.99 | 0.91 | 0.95 |
| 30 | 0.27 | 1.00 | 0.85 | 0.92 |
| 35 | 0.13 | 1.00 | 0.77 | 0.87 |
| 40 | 0.05 | 0.98 | 0.68 | 0.82 |
| 45 | 0.01 | 0.93 | 0.57 | 0.73 |
| 50 | 0.00 | 0.85 | 0.45 | 0.63 |
| 55 | 0.00 | 0.74 | 0.33 | 0.52 |
| 60 | 0.00 | 0.61 | 0.23 | 0.40 |
| 65 | 0.00 | 0.44 | 0.16 | 0.29 |
| 70 | 0.00 | 0.30 | 0.11 | 0.20 |
| 75 | 0.00 | 0.18 | 0.09 | 0.13 |
| 80 | 0.00 | 0.09 | 0.06 | 0.07 |
| 85 | 0.00 | 0.04 | 0.04 | 0.04 |
| 90 | 0.00 | 0.00 | 0.00 | 0.00 |

FIG. 6

| ANGLE θ | LIGHT GUIDE FIBER | ILLUMINATION OPTICAL SYSTEM 2a | ILLUMINATION OPTICAL SYSTEM 2b | COMBINED ILLUMINATION OPTICAL SYSTEM 2d |
|---|---|---|---|---|
| 0 | 1.00 | 1.00 | 1.00 | 1.00 |
| 5 | 0.97 | 1.01 | 0.99 | 1.00 |
| 10 | 0.94 | 0.99 | 0.98 | 0.98 |
| 15 | 0.85 | 0.98 | 0.97 | 0.97 |
| 20 | 0.67 | 0.98 | 0.95 | 0.96 |
| 25 | 0.46 | 0.99 | 0.91 | 0.93 |
| 30 | 0.27 | 1.00 | 0.85 | 0.89 |
| 35 | 0.13 | 1.00 | 0.77 | 0.84 |
| 40 | 0.05 | 0.98 | 0.68 | 0.77 |
| 45 | 0.01 | 0.93 | 0.57 | 0.67 |
| 50 | 0.00 | 0.85 | 0.45 | 0.57 |
| 55 | 0.00 | 0.74 | 0.33 | 0.45 |
| 60 | 0.00 | 0.61 | 0.23 | 0.34 |
| 65 | 0.00 | 0.44 | 0.16 | 0.24 |
| 70 | 0.00 | 0.30 | 0.11 | 0.17 |
| 75 | 0.00 | 0.18 | 0.09 | 0.12 |
| 80 | 0.00 | 0.09 | 0.06 | 0.07 |
| 85 | 0.00 | 0.04 | 0.04 | 0.04 |
| 90 | 0.00 | 0.00 | 0.00 | 0.00 |

FIG. 9

| ANGLE θ | LIGHT GUIDE FIBER | ILLUMINATION OPTICAL SYSTEM 2a | ILLUMINATION OPTICAL SYSTEM 2b | COMBINED ILLUMINATION OPTICAL SYSTEM 2e |
|---|---|---|---|---|
| 0 | 1.00 | 1.00 | 1.00 | 1.00 |
| 5 | 0.97 | 1.01 | 0.99 | 1.00 |
| 10 | 0.94 | 0.99 | 0.98 | 0.99 |
| 15 | 0.85 | 0.98 | 0.97 | 0.98 |
| 20 | 0.67 | 0.98 | 0.95 | 0.97 |
| 25 | 0.46 | 0.99 | 0.91 | 0.96 |
| 30 | 0.27 | 1.00 | 0.85 | 0.94 |
| 35 | 0.13 | 1.00 | 0.77 | 0.91 |
| 40 | 0.05 | 0.98 | 0.68 | 0.87 |
| 45 | 0.01 | 0.93 | 0.57 | 0.79 |
| 50 | 0.00 | 0.85 | 0.45 | 0.70 |
| 55 | 0.00 | 0.74 | 0.33 | 0.58 |
| 60 | 0.00 | 0.61 | 0.23 | 0.47 |
| 65 | 0.00 | 0.44 | 0.16 | 0.33 |
| 70 | 0.00 | 0.30 | 0.11 | 0.23 |
| 75 | 0.00 | 0.18 | 0.09 | 0.15 |
| 80 | 0.00 | 0.09 | 0.06 | 0.08 |
| 85 | 0.00 | 0.04 | 0.04 | 0.04 |
| 90 | 0.00 | 0.00 | 0.00 | 0.00 |

FIG. 10

| ANGLE θ | ILLUMINATION OPTICAL SYSTEM 2f | ILLUMINATION OPTICAL SYSTEM 2g | COMBINED ILLUMINATION OPTICAL SYSTEM 2h | COMBINED ILLUMINATION OPTICAL SYSTEM 2i | COMBINED ILLUMINATION OPTICAL SYSTEM 2j |
|---|---|---|---|---|---|
| 0 | 1.00 | 1.00 | 1.00 | 1.00 | 1.00 |
| 5 | 0.99 | 0.98 | 0.99 | 0.99 | 0.99 |
| 10 | 0.99 | 0.97 | 0.98 | 0.98 | 0.98 |
| 15 | 0.98 | 0.95 | 0.96 | 0.96 | 0.97 |
| 20 | 0.98 | 0.92 | 0.95 | 0.94 | 0.96 |
| 25 | 0.97 | 0.86 | 0.91 | 0.89 | 0.93 |
| 30 | 0.95 | 0.79 | 0.86 | 0.84 | 0.89 |
| 35 | 0.93 | 0.69 | 0.80 | 0.76 | 0.84 |
| 40 | 0.90 | 0.58 | 0.72 | 0.67 | 0.78 |
| 45 | 0.85 | 0.46 | 0.64 | 0.58 | 0.70 |
| 50 | 0.77 | 0.34 | 0.54 | 0.47 | 0.61 |
| 55 | 0.68 | 0.24 | 0.43 | 0.36 | 0.51 |
| 60 | 0.54 | 0.15 | 0.32 | 0.26 | 0.39 |
| 65 | 0.36 | 0.09 | 0.21 | 0.17 | 0.26 |
| 70 | 0.20 | 0.06 | 0.12 | 0.10 | 0.14 |
| 75 | 0.10 | 0.04 | 0.07 | 0.06 | 0.08 |
| 80 | 0.06 | 0.01 | 0.03 | 0.03 | 0.04 |
| 85 | 0.03 | 0.01 | 0.02 | 0.01 | 0.02 |
| 90 | 0.00 | 0.00 | 0.00 | 0.00 | 0.00 |

FIG. 11

| ANGLE θ | ILLUMINATION OPTICAL SYSTEM 2k | ILLUMINATION OPTICAL SYSTEM 2l | COMBINED ILLUMINATION OPTICAL SYSTEM 2m | COMBINED ILLUMINATION OPTICAL SYSTEM 2n |
|---|---|---|---|---|
| 0 | 1.00 | 1.00 | 1.00 | 1.00 |
| 5 | 1.00 | 1.00 | 1.00 | 1.00 |
| 10 | 0.99 | 0.98 | 0.98 | 0.98 |
| 15 | 0.99 | 0.94 | 0.96 | 0.95 |
| 20 | 0.99 | 0.90 | 0.94 | 0.92 |
| 25 | 1.00 | 0.85 | 0.92 | 0.89 |
| 30 | 1.00 | 0.80 | 0.89 | 0.86 |
| 35 | 0.99 | 0.74 | 0.85 | 0.81 |
| 40 | 0.98 | 0.66 | 0.80 | 0.75 |
| 45 | 0.95 | 0.57 | 0.73 | 0.67 |
| 50 | 0.90 | 0.46 | 0.65 | 0.58 |
| 55 | 0.83 | 0.35 | 0.56 | 0.49 |
| 60 | 0.74 | 0.25 | 0.46 | 0.39 |
| 65 | 0.63 | 0.17 | 0.37 | 0.30 |
| 70 | 0.50 | 0.11 | 0.28 | 0.22 |
| 75 | 0.37 | 0.07 | 0.20 | 0.15 |
| 80 | 0.24 | 0.04 | 0.13 | 0.10 |
| 85 | 0.14 | 0.03 | 0.07 | 0.06 |
| 90 | 0.00 | 0.00 | 0.00 | 0.00 |

ENDOSCOPE

TECHNICAL FIELD

The present invention relates to an ENDOSCOPE and, more particularly, to an ENDOSCOPE provided with a plurality of illumination optical systems in an insertion portion at a distal end thereof.

BACKGROUND ART

There are known endoscopes which include a plurality of illumination optical systems provided in an insertion portion at a distal end thereof, the illumination optical system having an illumination lens and a light guide fiber for guiding an illuminating light to the lens. When an endoscope is used in order to observe the inside of a body cavity, an insertion portion thereof is inserted into the body cavity, an illuminating light emitted from a light source is guided by a light guide fiber to the insertion portion, the guided illuminating light is dispersed by a lens to illuminate a site to be observed.

As such endoscopes, Japanese Unexamined Patent Application, Publication No. Hei10-288742 (PTL 1) discloses an endoscope provided with a plurality of illumination optical systems with one concave lens, in which each illumination optical system illuminates an inserting direction and a side of a distal end portion thereof respectively. Japanese Unexamined Patent Application, Publication No. 2006-72098 (PTL 2) discloses an endoscope in which an illumination optical system comprising one or three convex lenses and an illumination optical system comprising one aspheric convex lens are used in combination, as appropriate, to illuminate a site to be observed.

CITATION LIST

Patent Literature

{PTL 1}
  Japanese Unexamined Patent Application, Publication No. Hei10-288742
{PTL 2}
  Japanese Unexamined Patent Application, Publication No. 2006-72098

SUMMARY OF INVENTION

Technical Problem

Since the endoscope disclosed in PTL 1 uses only the concave lens, the illuminating light is sufficiently distributed in a distant view observation, while the entire range of field of view cannot be illuminated due to insufficient dispersion of the illuminating light in a near view observation. Since the endoscope disclosed in PTL 2 achieves the wide-range illumination by using an aspheric convex lens, the range of field of view can be sufficiently illuminated in a near view, while in a distant view observation, the illuminating light is not distributed to a site to be observed, thereby causing insufficient amount of light.

The present invention has been made in view of the above problems, and an object of the present invention is to provide an endoscope which can achieve the clear observation in the entire range from a near view to a distant view, by providing excellent illumination over the entire range from the near view to the distant view.

Solution to Problem

To achieve the above-described object, the present invention provides the following solutions.

An aspect of the present invention provides an endoscope which includes an imaging optical system provided in an insertion portion at a distal end of the endoscope and for observing an object to be observed, and a plurality of illumination optical systems provided in the insertion portion and for distributing the illuminating light emitted from a light source to the object to be observed, the illumination optical systems being directed in the same direction each other to illuminate the same field of view, wherein at least one of the plurality of illumination optical systems is a first illumination optical system having a convex lens, and at least one of the others is a second illumination optical system having a concave lens.

BRIEF DESCRIPTION OF DRAWINGS

FIG. 4 shows a light distribution table for the illumination optical systems applied to the endoscope according to the first embodiment of the present invention.

FIG. 6 shows a light distribution table for illumination optical systems applied to the endoscope according to the second embodiment of the present invention.

FIG. 9 shows a light distribution table for illumination optical systems applied to the endoscope according to the third embodiment of the present invention.

FIG. 10 shows a light distribution table of Reference Example 1 of the present invention.

FIG. 11 shows a light distribution table of Reference Example 2 of the present invention.

DESCRIPTION OF EMBODIMENTS (First Embodiment)

An endoscope according to a first embodiment of the present invention will now be described with reference to the accompanying drawings.

Figure 1:
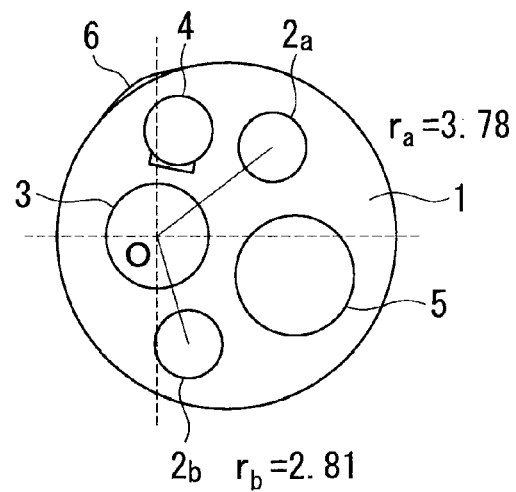
FIG. 1 is a schematic diagram showing a front face of a distal end of an insertion portion of an endoscope according to a first embodiment of the present invention.

FIG. 1 shows a front face of a distal end portion of an insertion portion 1 of the endoscope according to the present embodiment. The insertion portion 1 includes, as shown in FIG. 1, two illumination optical systems 2a, 2b which distribute the illuminating light emitted from a light source (not shown) and supplied through a light guide fiber 11, to the same field of view of an object to be observed, an imaging optical system 3 which picks up an image of an object to be observed, a nozzle 4 which supplies a lavage fluid and air to the imaging optical system 3, and a channel 5 from which a treatment appliance such as forceps and a probe is derived.

Figure 2:
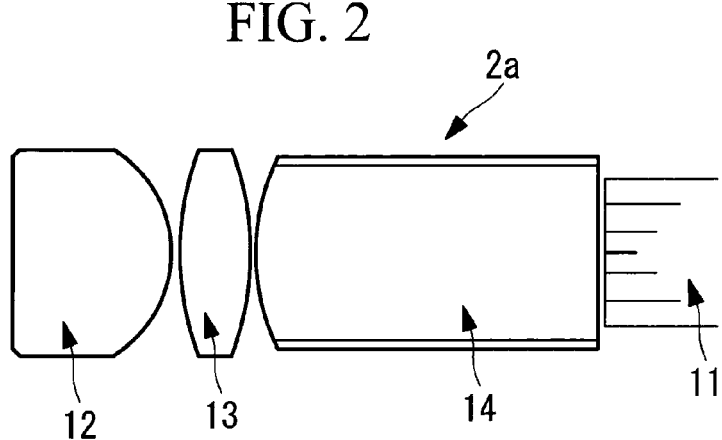
FIG. 2 is a side view showing a concave lens as an illumination optical system applied to the endoscope according to the first embodiment of the present invention.

The illumination optical system 2a includes, as shown in FIG. 2, a plano-convex lens 12, a biconvex lens 13, a glass rod 14, and the light guide fiber 11 which are arranged in parallel so that optical axes thereof are aligned toward a light source side (the middle right side of FIG. 2) from a front face side of the distal end portion (the middle left side of FIG. 2).

The plano-convex lens 12 is arranged so as to have a flat surface on the front face side of the distal end portion and a convex surface on the light source side. The magnitude of a radius of curvature $R_1$ of the plano-convex lens 12 satisfies the following Conditional Expression (1).

$$0.9 < R_1 f < 1.8 \quad (1)$$

where f is a focal length of the illumination optical system 2a.

By satisfying Expression (1), problems can be prevented from occurring due to too narrow or too wide light distribution range, and the illuminating light can be uniformly distributed over the entire range from a near view to a distant view.

In the present embodiment, a plano-convex lens with $R_1 = 1.007$ as the magnitude of the radius of curvature and made of glass with refractive index nd=1.88 is applied. A focal length of the illumination optical system 2a can be calculated as f=0.628 by using the magnitude of the radius of curvature $R_1$ and the refractive index nd=1.88. Accordingly, one obtains $R_1/f = 1.007/0.628 = 1.60$, and therefore the above Expression (1) is satisfied. Note that the focal length f here refers to a combined focal length of the plano-convex lens 12, the biconvex lens 13 and the glass rod 14.

The biconvex lens 13 is a so-called symmetrical biconvex lens, and radii of curvature $R_2$ of both surfaces thereof are equal in magnitude. The magnitude of the radii of curvature $R_2$ of the biconvex lens satisfies the following Conditional Expression (2) in the relationship with the radius of curvature $R_1$ of the plano-convex lens.

$$1.6 < R_2/R_1 < 3.2 \quad (2)$$

By satisfying Expression (2), problems can be prevented from occurring due to too narrow or too wide light distribution range, and the illuminating light can be uniformly distributed over the entire range from the near view to the distant view.

In the present embodiment, a biconvex lens with $R_2 = 2.579$ as the magnitude of the radius of curvature and made of glass with refractive index nd=1.88 is applied. Accordingly, one obtains $R_2/R_1 = 2.579/1.007 = 2.56$, and therefore the above Expression (2) is satisfied.

The glass rod 14 has a two-layer structure comprising a core in a center portion and a cladding covering the periphery of the core, the core having the refractive index nd=1.73 and the cladding having the refractive index nd=1.52.

Figure 3:
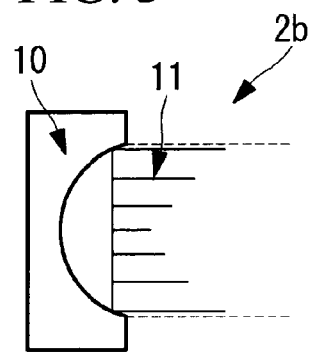
FIG. 3 is a side view showing a convex lens as the illumination optical system applied to the endoscope according to the first embodiment of the present invention.

The illumination optical system 2b includes, as shown in FIG. 3, one plano-concave lens 10 which has a flat surface on the front face side of the distal end portion (the middle left side of FIG. 3) and a concave surface on the light source side (the middle right side of FIG. 3), and the light guide fiber 11. In the plano-concave lens 10, a radius of curvature $R_3$ thereof satisfies the following Conditional Expression (3).

$$0.8 < R_3/D < 1.0 \quad (3)$$

where D is a lens radius. In the present embodiment, a plano-concave lens with D=1.7 and $R_3$=0.76 and with the refractive index nd=1.88 at the d-line is applied. Accordingly, one obtains $R_3/D = 0.76/0.85 = 0.89$, and therefore the above Expression (3) is satisfied. By satisfying Expression (3), the illuminating light can be well distributed while maintaining excellent workability of the concave lens.

The amount of light emitted by the illumination optical system 2a is set to be more than that emitted by the illumination optical system 2b, and the central illuminance by the illumination optical system 2b is set to be larger than that by the illumination optical system 2a. By doing so, the illuminating light from the illumination optical system 2b carries a long distance, thereby improving the light distribution performance in distant view observation.

In the imaging optical system 3, an angle of view thereof can take a value to satisfy the following Conditional Expression (4).

$$3 < \tan \omega_M < 14 \quad (4)$$

where $\omega_M$ is a maximum half angle of view of the imaging optical system 3. In the present embodiment, $\tan \omega_M$ is set to 6.5, and the above Expression (4) is satisfied. By satisfying Expression (4), even when a wide-angle imaging optical system is applied, the illuminating light can be well distributed over the range from the near view to the distant view.

Returning to FIG. 1, the illumination optical system 2a and the illumination optical system 2b are arranged so that the illumination optical system 2a is located more distantly than the illumination optical system 2b relative to a center O of the imaging optical system 3. That is, as shown in FIG. 1, a distance $r_a$ from the center O of the imaging optical system 3 to a center of the imaging optical system 2a is set to 3.78 mm and a distance $r_b$ from the center O of the imaging optical system 3 to a center of the imaging optical system 2b is set to 2.81 mm.

That is, the light from the illumination optical system 2a arranged most distantly in a radial direction from the imaging optical system is distributed over a wider range than that from the illumination optical system 2b arranged nearest to the imaging optical system.

By doing so, the halation is suppressed, and the illuminating light can be well distributed. That is, when the illumination optical system with wider light distribution is near the imaging optical system, especially when the illumination optical system is close to an object, the illuminating light is observed by the imaging optical system in a wider range, and therefore the occurrence of halation is increased. Accordingly, the halation is suppressed and the illuminating light can be well distributed by making the light distribution range of the illumination optical system arranged most distantly in a radial direction from the imaging optical system wider than that of the illumination optical system arranged nearest to the imaging optical system.

The imaging optical system 3 is arranged so as to satisfy the following Conditional Expression (5) in the relationship with the illumination optical systems 2a, 2b in the front face of the distal end portion of the insertion portion 1.

$$0.2 < r/\varnothing < 0.5 \quad (5)$$

where $r_a$ and $r_b$ are, in the front face of the distal end portion of the insertion portion 1, distances from the centers of the illumination optical systems 2a, 2b to the center of the imaging optical system 3, respectively, and $\varnothing$ is an outer diameter of the front face of the distal end portion of the insertion portion 1. In the present embodiment, $\varnothing$=8.6 mm. Here, the outer diameter of the front face of the distal end portion refers to a diameter of a circular part, without consideration of a protrusion portion 6 caused by physical structure in the insertion portion.

Accordingly, one obtains $r_a/\varnothing=3.78/8.6=0.44$ and $r_b/\varnothing=2.81/8.6=0.33$, and therefore the distances between the centers of the illumination optical systems 2a, 2b and the center of the imaging optical system 3 satisfy the above Expression (5). By arranging the plurality of illumination optical systems and an imaging optical system appropriately, the light distribution performance can be improved. That is, by satisfying the condition of Expression (5), the light distribution performance can be improved while physically preventing the imaging optical system and the plurality of illumination optical systems from interfering with the other structures such as a channel and a nozzle provided in the insertion portion and also preventing a diameter of a scope from being increased.

In the above Conditional Expression (5), when satisfying $$0.25 < r/\varnothing < 0.35 \tag{5a},$$

it is more preferable for the near view observation, when satisfying $$0.35 < r/\varnothing < 0.45 \tag{5b},$$

it is more preferable for the distant view observation.

The illumination optical systems 2a, 2b satisfy the following Conditional Expression (6) where the spherical light distribution illuminance function of the illumination optical system 2a is expressed as $\alpha(\theta)$ and the spherical light distribution illuminance function of the illumination optical system 2b is expressed as $\beta(\theta)$.

$$\alpha(60°)/\beta(60°) > 2 \tag{6}$$

where the spherical light distribution illuminance function $\alpha(\theta)$ is a function representing the illuminance when a spherical object is illuminated relative to the illumination optical system 2a. The function represents the illuminance distribution in a range of exit angle $\theta$ of the illumination optical system 2a where the illuminance is set to 1 when the exit angle $\theta$ from the center of the illumination optical system 2a is 0°. Similarly, the spherical light distribution illuminance function $\beta(\theta)$ is a function representing the illuminance when a spherical object is illuminated relative to the illumination optical system 2b. The function represents the illuminance distribution in a range of exit angle $\theta$ of the illumination optical system 2b where the illuminance is set to 1 when the exit angle $\theta$ from the center of the illumination optical system 2b is 0°. By satisfying Conditional Expression (6), the light distribution performance can be further improved in the range from the near view to the distant view. Note that when the resultant value falls outside the range of Conditional Expression (6), the light distribution difference from the illumination by the convex lens to the illumination by the concave lens becomes small, and any of appearances in the near view and the distant view becomes worse.

The illumination optical systems 2a, 2b satisfy the following Conditional Expression (7) where the spherical light distribution illuminance function of the combined illumination optical system combining the illumination optical systems 2a, 2b is expressed as $\gamma(\theta)$.

$$0.2 < \gamma(60°) < 0.5 \tag{7}$$

where the spherical light distribution illuminance function $\gamma(\theta)$ is a function representing the illuminance when a spherical object is illuminated relative to the combined illumination optical system. The function represents the illuminance distribution in a range of exit angle $\theta$ of the combined illumination optical system where the illuminance is set to 1 when the exit angle $\theta$ from the center of the combined illumination optical system is 0°. By satisfying Expression (7), the illuminating light can be distributed over the entire range of field of view while sufficiently maintaining the amount of light in the center portion of the range of field of view.

Note that, if the function $\gamma(\theta)$ is above the upper limit, the light distribution range is too wide and the central illuminance is reduced, if it is below the lower limit, the light distribution range is too narrow and the entire object to be observed cannot be illuminated. Therefore, by narrowing the range of Conditional Expression (7) described above, it is more preferable to satisfy $$0.25 < \gamma(60°) < 0.45 \tag{7a, and}$$

it is further preferable to satisfy $$0.30 < \gamma(60°) < 0.40 \tag{7b}.$$

FIG. 4 shows a light distribution table for the light guide fiber 11, the illumination optical systems 2a, 2b and the combined illumination optical system 2c of the illumination optical systems 2a, 2b in the insertion portion 1 of FIG. 1.

As shown in the light distribution table of FIG. 4, $$\alpha(60°)/\beta(60°) = 0.61/0.23 = 2.65, \text{ and}$$

$$\gamma(60°) = 0.40.$$

Accordingly, the illumination optical systems 2a, 2b and the combined illumination optical system 2c satisfy the above Conditional Expressions (6) and (7) at the edit angle $\theta=60°$ thereof.

Note that it is preferable that the spherical light distribution illuminance function $\alpha(\theta)$ of the illumination optical system 2a, which is an illumination optical system arranged most distantly in a radial direction from the imaging optical system, satisfy the following Conditional Expression.

$$\alpha(60°) > 0.5 \tag{8}$$

By doing so, the light distribution performance can be further improved in the near view. That is, in the light distribution performance in the near view, the entire screen can be brightly illuminated by arranging the illumination optical system with wide light distribution. Thus, by satisfying the above Conditional Expression (8), the light distribution performance can be further improved in the near view.

By doing so, both of the illumination optical system 2a having a convex lens and the illumination optical system 2b having a concave lens illuminate the same field of view of an object to be observed, and therefore the endoscope makes it possible to disperse and distribute the illuminating light over a wide range of the near view by using the convex lens of the illumination optical system 2a, and disperse the illuminating light over the relatively narrow range by using the concave lens of the illumination optical system 2b so as to sufficiently distribute the illuminating light to the distant view. Accordingly, regardless of the distance of an object to be observed from the insertion portion of the endoscope, excellent illumination over the entire range from the near view to the distant view can be achieved and clear observation can be achieved for the observation of the entire range from the near view to the distant view.

In addition, the number of refraction points for the illuminating light emitted from the light source is increased by arranging three convex lenses in parallel in the illumination optical system 2a, and therefore the illuminating light from the illumination optical system 2a can be widely distributed.

(Second Embodiment)

A second embodiment of the present invention will now be described. The difference between the present embodiment and the first embodiment described above is that two illumination optical systems are provided in the first embodiment, while three illumination optical systems are provided in the present embodiment. As a result, there are differences in a diameter of the insertion portion, the position relationship between the imaging optical system and the illumination optical systems, and the like. As for the other points, the components thereof are substantially the same as the first embodiment described above, and therefore, in the present embodiment, the same components as the first embodiment are denoted with the same reference signs and a description thereof will be omitted.

Figure 5:
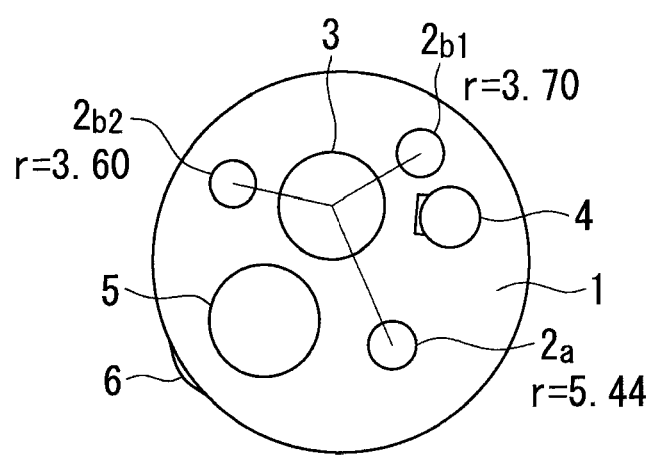
FIG. 5 is a schematic diagram showing a front face of a distal end of an insertion portion of an endoscope according to a second embodiment of the present invention.

An endoscope of the present embodiment includes, as shown in FIG. 5, one illumination optical system $2a$ and two illumination optical systems $2b_1$, $2b_2$.

The illumination optical system $2a$ includes, as shown in FIG. 2, a plano-convex lens, a biconvex lens, a glass rod, and a light guide fiber which are arranged in parallel so that optical axes thereof are aligned, and the refractive index, the radius of curvature and the like of each lens are similar to those for the illumination optical system $2a$ in the first embodiment.

The illumination optical systems $2b_1$, $2b_2$ includes, as shown in FIG. 3, one plano-concave lens and a light guide fiber, and the diameter, the refractive index and the radius of curvature of the lens are similar to those for the illumination optical system $2b$ in the first embodiment.

Accordingly, the illumination optical systems $2a$, $2b_1$, $2b_2$ satisfy the above Conditional Expressions (1) to (3).

The illumination optical systems $2a$, $2b_1$, $2b_2$ are arranged as follows. That is, the arrangement is provided in which the distance from a center O of an imaging optical system 3 to a center of the imaging optical system $2a$ is set as $r_a$=5.44 mm, the distance from the center O of the imaging optical system 3 to a center of the imaging optical system $2b_1$ is set as $r_{b1}$=3.70 mm, and the distance from the center O of the imaging optical system 3 to a center of the imaging optical system $2b_2$ is set as $r_{b2}$=3.60 mm, so that the illumination optical system $2a$ is located more distantly than the illumination optical systems $2b_1$, $2b_2$ relative to the center O of the imaging optical system 3.

An outer diameter of a front face of a distal end portion of an insertion portion 1 is set as Ø=13.2 mm. Accordingly, one obtains $r_a$/Ø=5.44/13.2=0.41, $r_{b1}$/Ø=3.70/13.2=0.28 and $r_{b2}$/Ø=3.60/13.2=0.28, and therefore the distances between the centers of the illumination optical systems $2a$, $2b_1$, $2b_2$ and the center of the imaging optical system 3 satisfy the above Expression (5).

FIG. 6 shows a light distribution table for a light guide fiber 11, the illumination optical systems $2a$, $2b_1$, $2b_2$ and a combined illumination optical system $2d$ of the illumination optical systems $2a$, $2b_1$, $2b_2$ in the insertion portion 1 of FIG. 5.

As shown in the light distribution table of FIG. 6, $$\alpha(60°)/\beta(60°)=0.61/0.23=2.65, \text{ and}$$

$$\gamma(60°)=0.34.$$

Accordingly, the illumination optical systems $2a$, $2b_1$, $2b_2$ and the combined illumination optical system $2d$ satisfy the above Conditional Expressions (6) and (7) at the edit angle θ=60° thereof.

By doing so, both of the illumination optical system $2a$ having three convex lenses and the illumination optical systems $2b$ each having a concave lens illuminate the same field of view of an object to be observed, and therefore the endoscope makes it possible to disperse and distribute the illuminating light over a wide range of the near view by using the convex lenses of the illumination optical system $2a$, and disperse the illuminating light over the relatively narrow range by using the concave lenses of the illumination optical systems $2b$ so as to sufficiently distribute the illuminating light to the distant view.

(Modified Example of Second Embodiment)

Figure 7:
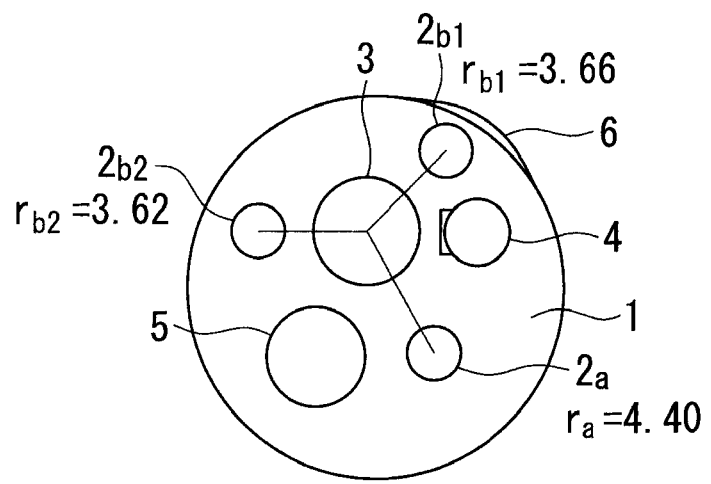
FIG. 7 is a schematic diagram showing a front face of a distal end of an insertion portion of an endoscope according to a Modified Example of the second embodiment of the present invention.

A Modified Example of the second embodiment described above will now be described. In the present Modified Example, as shown in FIG. 7, the outer diameter of the front face of the distal end portion of the insertion portion 1 differs from that in the second embodiment, and therefore the distances from the centers of the illumination optical systems $2a$, $2b_1$, $2b_2$ to the center O of the imaging optical system 3 differ from those in the second embodiment.

Specifically, the outer diameter of the front face of the distal end portion of the insertion portion 1 is set as Ø=11.7 mm, and the arrangement is provided in which the distance from the center O of the imaging optical system 3 to the center of the imaging optical system $2a$ is set to $r_a$=4.44 mm, the distance from the center O of the imaging optical system 3 to the center of the imaging optical system $2b_1$ is set to $r_{b1}$=3.66 mm, and the distance from the center O of the imaging optical system 3 to the center of the imaging optical system $2b_2$ is set to $r_{b2}$=3.62 mm.

Accordingly, one obtains $r_a$/Ø=4.44/11.7=0.38, $r_{b1}$/Ø=3.66/11.7=0.31 and $r_{b2}$/Ø=3.62/11.7=0.31, and therefore the distances between the centers of the illumination optical systems $2a$, $2b_1$, $2b_2$ and the center of the imaging optical system 3 satisfy the above Expression (5). A light distribution table in the present Modified Example is similar to that of FIG. 6, also in the present Modified Example, $$\alpha(60°)/\beta(60°)=0.61/0.23=2.65, \text{ and}$$

$$\gamma(60°)=0.47.$$

Accordingly, the illumination optical systems $2a$, $2b_1$, $2b_2$ and the combined illumination optical system $2d$ satisfy the above Conditional Expressions (6) and (7) at the edit angle θ=60° thereof.

Note that the light distribution table in the present Modified Example is similar to that of FIG. 6.

By doing so, both of the illumination optical system $2a$ having three convex lenses and the illumination optical systems $2b$ each having a concave lens illuminate the same field of view of an object to be observed, and therefore the endoscope makes it possible to disperse and distribute the illuminating light over a wide range of the near view by using the convex lenses of the illumination optical system $2a$, and disperse the illuminating light over the relatively narrow range by using the concave lenses of the illumination optical systems $2b$ so as to sufficiently distribute the illuminating light to the distant view.

(Third Embodiment)

A third embodiment of the present invention will now be described. The difference between the present embodiment and the second embodiment described above is that one illumination optical system $2a$ and two illumination optical systems $2b_1$, $2b_2$ are provided in the second embodiment, while two illumination optical systems $2a_1$, $2a_2$ and one illumination optical system $2b$ are provided in the present embodiment. In addition, there are differences in a diameter of the insertion portion, the position relationship between the imaging optical system and the illumination optical systems, and the like. As for the other points, the components thereof are substantially the same as the first embodiment and the second embodiment described above, and therefore, in the present embodiment, the same components as the embodiments described above are denoted with the same reference signs and a description thereof will be omitted.

Figure 8:
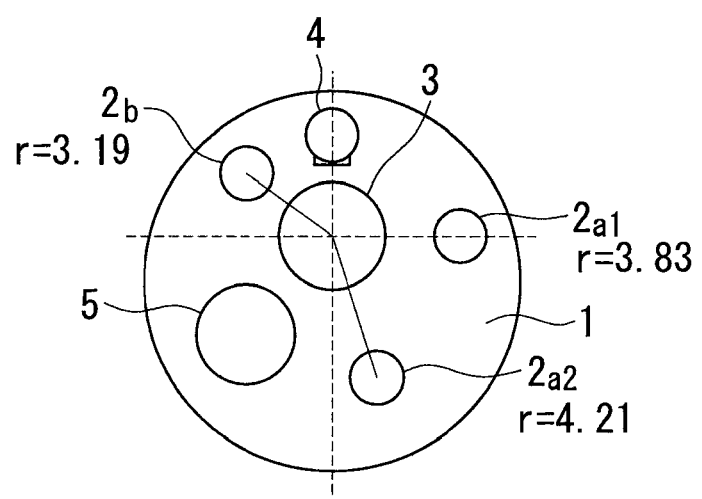
FIG. 8 is a schematic diagram showing a front face of a distal end of an insertion portion of an endoscope according to a third embodiment of the present invention.

An endoscope of the present embodiment includes, as shown in FIG. 8, two illumination optical systems $2a_1$, $2a_2$ and one illumination optical system $2b$.

The illumination optical systems $2a_1$, $2a_2$ each include, as shown in FIG. 2, a plano-convex lens, a biconvex lens, a glass rod, and a light guide fiber which are arranged in parallel so that optical axes thereof are aligned, and the refractive index, the radius of curvature and the like of each lens are similar to those for the illumination optical system $2a$ in the first embodiment.

The illumination optical system $2b$ includes, as shown in FIG. 3, one plano-concave lens and a light guide fiber, and the diameter, the refractive index and the radius of curvature of the lens are similar to those for the illumination optical system $2b$ in the first embodiment.

Accordingly, the illumination optical systems $2a_1$, $2a_2$, $2b$ satisfy the above Conditional Expressions (1) to (3).

The illumination optical systems $2a_1$, $2a_2$, $2b$ are arranged as follows. That is, the arrangement is provided in which the distance from a center O of an imaging optical system 3 to a center of the imaging optical system $2a_1$ is set as $r_{a1}=3.83$ mm, the distance from the center O of the imaging optical system 3 to a center of the imaging optical system $2a_2$ is set as $r_{a2}=4.21$ mm, and the distance from the center O of the imaging optical system 3 to a center of the imaging optical system $2b$ is set as $r_b=3.19$ mm, so that the illumination optical systems $2a_1$, $2a_2$ are located more distantly than the illumination optical system $2b$ relative to the center O of the imaging optical system 3.

An outer diameter of a front face of a distal end portion of an insertion portion 1 is set as $\varnothing=10.9$ mm. Accordingly, one obtains $r_{a1}/\varnothing=3.83/10.9=0.35$, $r_{a2}/\varnothing=4.21/10.9=0.39$ and $r/\varnothing=3.19/10.9=0.29$, and therefore the distances between the centers of the illumination optical systems $2a_1$, $2a_2$, $2b$ and the center of the imaging optical system 3 satisfy the above Expression (5).

FIG. 9 shows a light distribution table for a light guide fiber 11, the illumination optical systems $2a_1$, $2a_2$, $2b$ and a combined illumination optical system $2e$ of the illumination optical systems $2a_1$, $2a_2$, $2b$, in the insertion portion 1 of FIG. 8.

As shown in the light distribution table of FIG. 9, $\alpha(60°)/\beta(60°)=0.61/0.23=2.65$, and $\gamma(60°)=0.47$.

Accordingly, the illumination optical systems $2a_1$, $2a_2$, $2b$ and the combined illumination optical system $2e$ satisfy the above Conditional Expressions (6) and (7) at the edit angle $\theta=60°$ thereof.

By doing so, both of the illumination optical systems $2a$ each having three convex lenses and the illumination optical system $2b$ having a concave lens illuminate the same field of view of an object to be observed, and therefore the endoscope makes it possible to disperse and distribute the illuminating light over a wide range of the near view by using the convex lenses of the illumination optical systems $2a$, and disperse the illuminating light over the relatively narrow range by using the concave lens of the illumination optical system $2b$ so as to sufficiently distribute the illuminating light to the distant view.

Reference Example 1

As a Reference Example, it presents a case where an illumination optical system $2f$ comprising three convex lenses and with a radius of curvature of a plano-convex lens of the illumination optical system $2a$, $R_1=1.298$, and an illumination optical system $2g$ with a radius of curvature of a plano-concave lens of the illumination optical system $2b$, $R_3=0.84$, are applied.

In this case, $R_1/f=1.298/0.688=1.89$, $R_2/R_1=2.579/1.298=1.99$, and $R_3/D=0.84/0.85=0.99$.

Accordingly, the above Conditional Expressions (1) to (3) are satisfied.

FIG. 10 shows a light distribution table for the illumination optical system $2f$, the illumination optical system $2g$ and combined illumination optical systems combining these.

As shown in this light distribution table, $\alpha(60°)/\beta(60°)=0.54/0.15=3.6$.

Accordingly, the illumination optical system $2f$ and the illumination optical system $2g$ satisfy the above Conditional Expression (6).

Combined illumination optical systems $2h$, $2i$, $2j$ shown in this light distribution table are a combined illumination optical system provided with one illumination optical system $2f$ and one illumination optical system $2g$, a combined illumination optical system provided with one illumination optical system $2f$ and two illumination optical systems $2g$, and a combined illumination optical system provided with two illumination optical systems $2f$ and one illumination optical system $2g$, respectively.

That is, $\gamma_{2f}(60°)=0.32$ $\gamma_{2g}(60°)=0.26$ $\gamma_{2i}(60°)=0.39$.

Accordingly, each of the combined illumination optical systems $2f$, $2g$, $2j$ satisfies the above Conditional Expression (7).

Reference Example 2

As a Reference Example, it presents a case where an illumination optical system $2k$ comprising three convex lenses and with a radius of curvature of a plano-convex lens of the illumination optical system $2a$, $R_1=0.84$, and an illumination optical system $2l$ with a radius of curvature of a plano-concave lens of the illumination optical system $2b$, $R_3=0.703$, are applied.

In this case, $R_1/f=0.84/0.584=1.44$, $R_2/R_1=2.579/0.84=3.07$, and $R_3/D=0.703/0.85=0.83$.

Accordingly, the above Conditional Expressions (1) to (3) are satisfied.

FIG. 11 shows a light distribution table for the illumination optical system $2l$, the illumination optical system $2k$ and combined illumination optical systems combining these.

As shown in this light distribution table, $\alpha(60°)/\beta(60°)=0.74/0.25=2.96$.

Accordingly, the illumination optical system $2l$ and the illumination optical system $2k$ satisfy the above Conditional Expression (6).

Combined illumination optical systems $2m$, $2n$ shown in this light distribution table are a combined illumination optical system provided with one illumination optical system $2k$ and one illumination optical system $2l$ and a combined illumination optical system provided with one illumination optical system $2k$ and two illumination optical systems $2l$, respectively.

That is, $$\gamma_{2m}(60°)=0.46$$

$$\gamma_{2n}(60°)=0.39.$$

Accordingly, each of the combined illumination optical systems $2m$, $2n$ satisfies the above Conditional Expression (7).

REFERENCE SIGNS LIST

1 Insertion portion
2 Illumination optical system
3 Imaging optical system
4 Nozzle
5 Channel
6 Protrusion portion
10 Plano-concave lens
11 Light guide fiber
12 Plano-convex lens
13 Biconvex lens
14 Glass rod

The invention claimed is:

1. An endoscope comprising:
an imaging optical system provided at a distal end of an insertion portion of the endoscope and for observing an object to be observed; and
a plurality of illumination optical systems provided in the insertion portion and for distributing an illuminating light emitted from a light source to the object to be observed,
wherein at least one of the plurality of illumination optical systems is a first illumination optical system having a convex lens, and at least one of the others is a second illumination optical system having a concave lens,
wherein the first illumination optical system is directed in a same direction as a direction in which the second illumination optical system is directed, emits the illuminating light in a same direction as a direction in which the second illumination optical system emits the illuminating light, and distributes the illuminating light toward a same field of view as a field of view toward which the second illumination optical system distributes the illuminating light,
wherein a light distribution characteristic of the first illumination optical system is different from a light distribution characteristic of the second illumination optical system, and
wherein the following Conditional Expression is satisfied where a spherical light distribution illuminance function of the first illumination optical system is expressed as $\alpha(\theta)$ and a spherical light distribution illuminance function of the second illumination optical system is expressed as $\beta(\theta)$:

$$\alpha(60°)/\beta(60°)>2 \quad (1)$$

where the spherical light distribution illuminance function $\alpha(\theta)$ is a function representing illuminance when a spherical object is illuminated relative to the first illumination optical system, and the function represents illuminance distribution in a range of exit angle $\theta$ of the first illumination optical system where the illuminance is set to 1 when the exit angle $\theta$ from a center of the first illumination optical system is 0°; and where a spherical light distribution illuminance function $\beta(\theta)$ is a function representing illuminance when a spherical object is illuminated relative to the second illumination optical system, and the function represents illuminance distribution in a range of exit angle $\theta$ of the second illumination optical system where the illuminance is set to 1 when the exit angle $\theta$ from a center of the second illumination optical system is 0°.

2. The endoscope according to claim 1, wherein the first illumination optical system has three convex lenses.

3. The endoscope according to claim 1 comprising:
one first illumination optical system; and
two second illumination optical systems.

4. The endoscope according to claim 1,
wherein the plurality of illumination optical systems further include another first illumination optical system or another second illumination optical system, and
the first illumination optical system or the another first illumination optical system among the plurality of illumination optical systems is arranged most distantly in a radial direction from the imaging optical system in a distal end face of the insertion portion.

5. The endoscope according to claim 1,
wherein central illuminance of the second illumination optical system is larger than central illuminance of the first illumination optical system.

6. The endoscope according to claim 1,
wherein, in the distal end face of the insertion portion, a light from an illumination optical system arranged most distantly in a radial direction from the imaging optical system is distributed over a wider range than a light from an illumination optical system arranged nearest to the imaging optical system among the plurality of illumination optical systems.

7. The endoscope according to claim 3,
wherein the imaging optical system and each of the plurality of illumination optical systems are arranged so as to satisfy the following Conditional Expression in the distal end face of the insertion portion:

$$0.2<r/\emptyset<0.5 \quad (2)$$

where r is, in the distal end face of the insertion portion, a distance between a center of each of the illumination optical systems and a center of the imaging optical system, and $\emptyset$ is an outer diameter of the distal end face of the insertion portion.

8. The endoscope according to claim 3,
wherein the following Conditional Expression is satisfied where a spherical light distribution illuminance function of a combined illumination optical system combining the plurality of illumination optical systems is expressed as $\gamma(\theta)$:

$$0.2<\gamma(60°)<0.5 \quad (4)$$

where the spherical light distribution illuminance function $\gamma(\theta)$ is a function representing illuminance when a spherical object is illuminated relative to the combined illumination optical system, and the function represents illuminance distribution in a range of exit angle $\theta$ of the combined illumination optical system where the illuminance is set to 1 when the exit angle $\theta$ from a center of the combined illumination optical system is 0°.

9. The endoscope according to claim 3,
wherein the first illumination optical system includes a plano-convex lens and a biconvex lens in order from a distal end face side of the insertion portion, and magnitude of a radius of curvature $R_1$ of the plano-convex lens satisfies the following Conditional Expression:

$$0.9 < R_1/f < 1.8 \quad (5)$$

where f is a focal length of the first illumination optical system.

10. The endoscope according to claim 4, wherein an amount of light emitted by the first illumination optical system is more than an amount of light emitted by the second illumination optical system.

11. The endoscope according to claim 6,
wherein a spherical light distribution illuminance function $f(\theta)$ of an illumination optical system arranged most distantly in the radial direction of the imaging optical system satisfies the following Conditional Expression:

$$f(60°) > 0.5 \quad (8)$$

where the spherical light distribution illuminance function $f(\theta)$ represents illuminance when a spherical object is illuminated relative to the illumination optical system, and the function represents illuminance distribution in a range of exit angle $\theta$ of the illumination optical system where the illuminance is set to 1 when the exit angle $\theta$ from a center of the illumination optical system is 0°.

12. The endoscope according to claim 7,
wherein an angle of view of the imaging optical system satisfies the following Conditional Expression:

$$3 < \tan \omega_M < 14 \quad (3)$$

where $\omega_M$ is a maximum half angle of view of the imaging optical system.

13. The endoscope according to claim 9,
wherein radii of curvature $R_2$ of both surfaces of the biconvex lens are equal, and the magnitude of the radii of curvature $R_2$ satisfies the following Conditional Expression:

$$1.6 < R_2/R_1 < 3.2 \quad (6).$$

14. The endoscope according to claim 9,
wherein a radius of curvature $R_3$ of a surface of the concave lens on the light source side of the second illumination optical system satisfies the following Conditional Expression:

$$0.8 < R_3/D < 1.0 \quad (7)$$

where D is a lens radius of the concave lens.

\* \* \* \* \*